(12) United States Patent
Ledezma (10) Patent No.: US 6,582,693 B2
(45) Date of Patent: Jun. 24, 2003

(54) RECOMBINANT MVA VIRUS EXPRESSING THE E2 GENE OF BOVINE PAPILLOMAVIRUS AND ITS USE IN THE THERAPY OF TUMORS GENERATED BY PAPILLOMAVIRUSES

(75) Inventor: Ricardo R. Ledezma, Unidad Santa Fe (MX)

(73) Assignee: Lemery, S.A. de C.V., Col. Huichapan (MX)

( * ) Notice: Subject to any disclaimer, the term of this patent is extended or adjusted under 35 U.S.C. 154(b) by 0 days.

(21) Appl. No.: 09/866,726

(22) Filed: May 30, 2001

(65) Prior Publication Data

US 2002/0028498 A1 Mar. 7, 2002

Related U.S. Application Data

(63) Continuation-in-part of application No. 09/449,493, filed on Nov. 29, 1999, now abandoned.

(30) Foreign Application Priority Data

Nov. 30, 1998 (MX) .............................................. 9810026

(51) Int. Cl.[7] ...................... A61K 48/00; A61K 39/285; A61K 35/76; C12N 7/01; C12N 15/863
(52) U.S. Cl. ................ 424/93.2; 424/199.1; 424/204.1; 435/235.1; 435/320.1; 435/477
(58) Field of Search ........................... 435/235.1, 320.1, 435/477; 424/93.2, 199.1, 204.1

(56) References Cited

U.S. PATENT DOCUMENTS 5,185,146 A * 2/1993 Altenburger .............. 424/199.1
5,744,133 A * 4/1998 Lathe et al. ................ 424/93.2

FOREIGN PATENT DOCUMENTS

WO          9813500          4/1998

OTHER PUBLICATIONS

Guerrino Meneguzzi et al., Vaccine, vol. 8, Jun. 1990, pp. 199–204.
Ramaiah Selvakumar et al., Journal of Virology, vol. 69, No. 1, Jan. 1995, pp. 602–605.
Grun et al., Virology, vol. 158, No. 1, May 1987, pp. 28–33, abstract only.

* cited by examiner

Primary Examiner—Mary E. Mosher
(74) Attorney, Agent, or Firm—Birch, Stewart, Kolasch & Birch, LLP (57) ABSTRACT

A recombinant vaccinia virus derived from the vaccinia virus Ankara (MVA) encoding and capable of expressing the E2 gene of Bovine papillomavirus. Also, the use of the virus in the treatment of lesions caused by papillomavirus.

14 Claims, 9 Drawing Sheets

RECOMBINANT MVA VIRUS EXPRESSING THE E2 GENE OF BOVINE PAPILLOMAVIRUS AND ITS USE IN THE THERAPY OF TUMORS GENERATED BY PAPILLOMAVIRUSES

This application is a continuation-in-part of application Ser. No. 09/449,493 filed on Nov. 29, 1999, now abandoned, the entire contents of which are hereby incorporated by reference.

The present invention relates to recombinant vaccinia virus derived from the vaccinia virus Ankara (MVA) encoding and capable of expressing the E2 gene of Bovine papillomavirus, and the use of such recombinant in the treatment of lesions caused by papillomaviruses.

BACKGROUND OF THE INVENTION

Cervical Carcinoma

In man neoplasic transformation has been linked to the presence of papillomaviruses. They can induce diseases, from warts up to condilomas, and lesions, which can progress to malignant neoplasias. Approximately one million people get infected with papilloma virus every year, and in developing countries 50,000 women die annually due to cervical cancer.

In humans, it is well known that cervical cancer correlates with the presence of human papillomavirus (HPVS) particularly types 16, 18, 31, 33 and 35[3,4,5,6,7,8,9,10,11]. In contrast, HPV types 6, 11, 42, 43 are found only in the anogenital tract and are not associated with cervical cancer[3, 7, 12, 13].

Cervical carcinoma is the second most common cancer among women worldwide. More than 95% of all cervical carcinomas contain DNA of some papillomavirus (HPV)[3] with types 16 or 18 accounting for about 50% and 30% of all cases, respectively.

Most benign lesions (papillomas) generally regress on their own, but in some cases, some of them undergo malignant transformation. Papillomavirus are also found infecting a wide variety of vertebrates, and it has been described that they produce tumors in these animals as well[4,5,6,7,14].

Normally human papillomavirus infects and replicates in the form of an unintegrated circular episome in keratinocytes of genital mucosa and perigenital skin. The papillomavirus E2 and E1 gene products regulate viral DNA replication. The E2 gene product can also activate or repress transcription of different HPVs promoters[15,16]. In particular, the papillomavirus protein E2 is known to down regulate the P105 promoter, from HPV18, which controls transcription of the E6 and E7 oncogenes, which are expressed in a variety of cervical human tumors. The best studied HPVs, types 16 and 18 persist extracromosomally in precancerous lesions, but frequently get integrated into the cellular genome of cancer cells[16]. This event makes the papillomavirus E2 gene disrupted or inactivated leading to a derepression of the E6 and E7 oncogenes. Expression of these oncogenes appears to be a critical step in the maintenance of the transformed stage and progression to invasive carcinoma. This mechanism, however, is not necessarily the only one operating to induce the malignant stage, as suggested by recent studies where HPV integration was not detected in at least 30% of the analyzed cancers[13,17].

Since cervical cancer is a serious health problem and because there is a strong dependence with the infection by HPV, it is thought that the induction of a protective stage against these viruses would help in preventing the appearance of cervical tumors. Based on this idea, different strategies to develop a safe vaccine or immunotherapeutic agent against cervical cancer have been tried. Other methods, such as radiotherapy and chemotherapy have, of course been used to reduce papillomas, and cancer tumors. However, these methods work only efficiently during the first stages of tumor development. At later times it becomes very difficult to treat cervical tumors because of the tumor size and the side effects that anti-cancer drugs may have.

Because of the strong relationship between HPV infection and cervical cancer, many approaches have been tried in an effort to develop a successful therapy for cervical cancer. It has been shown that antisense oligonucleotides from partial or complete full-end clones of E6 and E7 genes are able to inhibit tumor cell growth in vitro and in vivo[18,19,20] by down regulating the E6 and E7 oncogenes. Cloned antigens, recognized by therapeutic antitumor lymphocytes (TAA), such as the B7-1 or B7-2 molecules, have been used in the construction of recombinant anticancer vaccines[21].

Using a recombinant vaccinia virus expressing the B7-1 molecule, it was found that the number of pulmonary metastases decreased in mice bearing tumor[21]. These molecules interact wit the T lymphocyte ligands CD28 and CTLA-4, and initiate a cascade of effects mediated, at least in part by up-regulation of interleukin 2 production[22,23,24].

The findings that the E2 protein of papillomavirus is capable of promoting cell growth arrest and stopping cell proliferation by inducing apoptosis of human cancer cells[15, 25,26], and that immunized animals with recombinant E2 proteins are capable of inducing tumor regression and decreasing the number of new papilloma foci formed[27], have lead to a novel approach for cervical cancer therapy. Namely, the introduction of the E2 gene into vaccinia virus was to efficiently direct the E2 protein against HPV tumors.

Inserting an antigen in a vaccinia virus (poxyirus) increases the expression of this molecule in the infected cell, therefore stimulating more efficiently the immune system[28, 29]. The purpose of using different antigens expressed in vaccinia virus is to try to enhance the immune response against these specific antigens. For these reasons it is thought that recombinant poxvirus are excellent candidates for a new type of vaccine and also for new therapeutic strategies.

Knowing these difficulties to treat cervical cancer it was decided to use an attenuated vaccinia virus known as Modified Vaccinia Ankara (MVA). This virus was developed and tested as a safe smallpox vaccine[30]. It was also found to be a virulent for normal or immunosuppressed animals, without side-effects in 120,000 humans inoculated for priming vaccination[30,31,32]. One reason that makes the MVA very safe is that viral expression and recombinant mechanisms are impaired for this virus. It has also been demonstrated that MVA is an excellent vector for expressing foreign genes, such as the *Escherichia coli* Lac Z or the page T7 polymerase[33,34] in infected cells. Moreover, MVA is capable of infecting most, if not all, the human cell lines tested up to now. Because of these characteristics, at the present time, the most successful strategy for vaccine development involves the use of vaccinia virus vectors.

This approach has already been used to protect animals against polyoma virus (PY) infection[35]. In these reports, it was demonstrated that treatment of rats with live recombinant vaccinia viruses expressing tumor-specific antigens from PY could prevent cognate tumor development and in some cases could also induce regression of preexisting tumors. Also an MVA recombinant virus expressing the haemaglutinin and nucleoprotein genes (HA and NP, respectively) of influenza virus (A/PR/8/34HA) was found to fully protect mice against a lethal influenza virus challenge[36].

According to the invention, a DNA sequence which codes for the E2 gene of Bovine papillomavirus is introduced using DNA recombination techniques within a naturally occurring DNA sequence of the MVA genome which is non-essential for virus replication. This recombinant virus will be helpful for the therapy of lesions induced by papillomaviruses.

OBJECT OF THE INVENTION

The present invention is to provide a recombinant MVA virus that expresses a papillomavirus antigen and is used as a therapeutic method to treat lesions generated by papillomaviruses.

SUMMARY OF THE INVENTION

The scope of this invention covers the necessary methods and the technology to express a specific gene in a viral expression vector (vaccinia virus strain MVA) specifically in a recombinant viral vector that carries the E2 gene of the bovine papilloma virus. This recombinant vector is capable of efficiently expressing the E2 gene inside any mammalian cell as well as in chicken fibroblast cells.

The recombinant MVA E2 virus as designed basically to be used in the therapeutic treatment of early/late lesions that are produced by infections with papilloma virus capable of generating tumors. This virus was mainly designed to inoculate directly into lesions produced by human papilloma virus.

The MVA E2 virus can be used in the elimination of pre-cancer lesions and has potential use in the elimination of viruses that provoke these lesions. The MVA E2 virus can be used in the treatment of lesions produced by any type of oncogene virus. The MVA E2 virus can be used in the regression of pre-cancerous lesions. The MVA E2 virus has the capacity to induce regression of cancer tumors.

Specific Points of the Invention

A recombinant MVA containing and capable of expressing a DNA sequence encoding a Bovine papillomavirus protein.

A recombinant MVA as above containing and capable of expressing DNA sequence of the E2 gene of Bovine papillomavirus.

DNA sequences are inserted at the site of naturally occurring deletions within MVA genome.

A recombinant MVA according as above, wherein the DNA sequences encoding antigen is under transcriptional control of the vaccinia virus early/late promoter P7.5.

A recombinant MVA as above and a pharmaceutically acceptable carrier or diluent.

A recombinant MVA as above containing and MVA encoding a Bovine papillomavirus antigen, and a pharmaceutically acceptable carrier or diluent.

A method for the treatment of all type of lesions generated by papillomavirus infections comprising administering to a living animal body, including a human, in need thereof a therapeutically effective amount of a recombinant MVA as above.

A method of treating a tumor lesion as above, comprising administering directly to the tumor a recombinant MVA expressing the E2 gene of Bovine papillomavirus.

A method of inducing anti-tumor antibodies in a tumor-bearing animal, comprising administering a recombinant MVA as above.

The Present Invention

The present invention relates to recombinant MVA that contain the E2 gene of bovine papillomavirus suitable in a physiologically acceptable form for the therapy of lesions caused by papillomaviruses. The invention also relates to methods for the preparation of such recombinant MVA virus.

Because it has been reported that the tumor growth can be reduced if sufficient amount of E2 protein is inside the cells[38], and recent experiments have showed that MVA recombinant virus carrying the E2 gene of bovine papillomarvirus is capable of stopping human tumor growth generated in nude mice by down regulating the expression of the E6 and E7 oncogenes and also generated apoptosis through P53 pathway. In this patent it is explored the therapeutic potential of recombinant vaccinia expressing the E2 gene of papillomavirus (MVA E2) in the treatment of an established tumor.

It was found in the MVA E2-treated animals that tumors stop growing, while in animals treated with MVA or PBS tumors continue (to grow. The MVA E2-treated animals presented complete tumor regression and were free of tumors for more than a year. A strong immune response was generated against vaccinia and E2 papilloma proteins as indicated by the presence of antibodies against these molecules. No evidence for complement-mediated or lymphocyte-mediated cytotoxicity of tumor cells was found. However, in tumor bearing rabbits treated with the MVA E2 virus, we also found large amounts of anti-tumor antibodies. These antibodies were capable of stimulating macrophages for efficient killing of tumor cells. These data strongly suggest that MVA E2-treated rabbits produce anti-tumor antibodies that stimulate macrophage antibody-dependent tumor cytotoxicity[39].

Based on this strategy, we decided to investigate the use of a recombinant MVA virus for therapeutic treatment of cervical cancer. Because the E2 protein represses expression of E6 and E7 proteins, and recent experiments showed that the E2 protein can also induce P53-mediated apoptosis in HeLa cells, and cell growth arrest independently of the transcriptional repression of the endogenous viral E6 and E7 genes[11,15,26], we decided to construct a MVA recombinant virus by inserting the E2 gene into the MVA genome. The new recombinant virus was named MVA E2 and its effects over human tumor growth in immunosuppressed animals were investigated.

In our experimental work, it was found that treatment with the recombinant MVA E2 virus resulted in tumor growth arrest in tumor-bearing mice. In contrast, only a slight inhibition of tumor growth was observed in animals inoculated with the parenteral MVA virus, and in control animals, just inoculated with PBS, the tumors continued to grow indefinitely. In addition, MVA E2 was capable of inducing strong tumor regression in tumor-bearing rabbits up to complete disappearance of the malignant tumor.

These data indicate that the recombinant MVA E2 has the capacity of inducing tumor elimination in animals and therefore it is a potential new therapeutic agent for cancer treatment[38].

Extract of the Invention:

A method is described to produce an expression viral vector with the recombinant vaccinia virus with the capacity to express the E2 gene of bovine papilloma virus in mammalian cells and in chicken embryo fibroblasts. The method includes the construction of the recombinant transfer vector through the insertion of a fragment of DNA (promoter of the vaccinia virus P7.5 E/L) and with the later insertion of a selected gene (E2 gene of bovine papilloma virus), so the new cloning vector is under the transcriptional control of promoter P7.5 E/L. The recombinant transfer vector is put in contact with DNA of the vaccinia virus to carry-out the recombination and the incorporation of the selected gene into the genome of the vaccinia virus. The recombinant vaccinia virus that results from this construction is used then to infect mammalian cells or chicken fibroblast cells in culture and, as a product of the infection, the protein of E2 gene is produced because it was selected and incorporated into the DNA of the vaccinia virus.

The recombinant virus produced as described above is named MVA E2, it is purified until it reaches 97% of purity, and then can be used in the treatment of early lesions as well as in preexisting tumors that have originated by any type of oncogenic papilloma virus. The invention of this recombinant virus will facilitate the therapeutic treatment of pre-cancer and cancer lesions as well as of present papillomas.

It has been proven that the recombinant virus MVA E2 can reduce and eliminate tumors, both in immunocompetent animals as well in those that do not have present an immune system (mice and rabbits). The MVA E2 virus has a high potential to eradicate oncogenic papilloma viruses and this is mainly due to the fact that recombinant virus MVA E2 can generate apoptosis in tumoral cells and also can cause a strong immune response directed towards cells that carry the papilloma virus. It has been also found that the virus MVA E2 generates a favorable cellular immune response mediated mainly by macrophages, which depend on antibodies that are capable of destroying cancer cells, which carry DNA of oncogenic papilloma viruses.

The MVA E2 virus also generates an immune response against the tumoral antigens, which causes that the pre-cancer lesions can be eliminated efficiently.

Reasons of using MVA are:

The MVA virus has a deletion of 30,000 bp of DNA compared with the wild type vaccinia, is highly attenuated, expressed foreign genes efficiently and does not show any side effects when used with humans in vaccination protocols.

Background:

Recent advances in recombinant DNA technology have facilitated the isolation of specific genes or of part of them and their transfer to bacteria, yeast, plant cells, animal cells, or to viruses that infect these organisms. The material of the transferred gene (either a native gene or a modified gene) is duplicated and propagates when the viruses duplicate or the transformed cells grow. As a result, the transformed cells have the capacity to synthesize the product that has been codified in the sequences of the transferred gene.

The transfer and expression of genes or portions of them among viruses, eucariotic cells and procariotic cells is possible due to the fact that the DNA of all living organisms is chemically similar and it is composed of the same four nucleotides. The basic differences are based on the nucleotide sequence that appears in the genome of the organisms. The specific nucleotide sequence arranged as codons (three nucleotides) codify for specific sequences of aminoacids. On the other hand the codification between the amino acid sequence and the nucleotide sequence of DNA is essentially the same for all organisms[1].

The genomic DNA is organized in sequences that codify for proteins (structural genes) and control regions (these are DNA sequences that control the initiation of the transcription phase and are usually known as promoters) that regulate the expression of structural genes. In general the RNA polymerase is activated in the region of the promoter and transcribes the information along the structural gene to a messenger RNA (mRNA). The mRNA contains recognition sequences, which are the signals for union to the ribosome and signals for the initiation and termination of the protein synthesis (translation). The recent advances on the genetic analysis of the role that play the transcriptional signals in the promoter regions of the genes (that are described usually as the region of 5' of the genes) have facilitated the possibility of removing and selectively alter the sequence of DNA with the purpose to study its function and its role in the expression of genes and to take certain sequences to study its function in heterologous biological systems such as the system host-vector of recombinant DNA technology[1].

The promoters in eucariotic organisms are usually characterized by their content of conserved nucleotides sequences that have structural similarity to the sequences of the promoters of procariotic organisms and this also suggests that they are involved in the regulation of the transcription process. The first of these sequences is rich in adenine and thymine (the position is classified as TATA), which is located 20–30 base pairs up stream from the initiation point of RNA (this site is where the transcription for mRNA initiates) and it is characterized because it contains the consensus sequence (5"TATAA-ATA-3'). The second consensus sequence it is localized 70–90 base pairs up stream and presents the consensus sequence 5'-GG(C/T)CAATCT-3'. All these sequences can be genetically manipulated and be used for the insertion of specific genes. Also these sequences can be altered by other techniques such as directed mutagenesis[1].

The restriction enzymes that are used for cloning of genes are specific proteins that cut the nucleic acids in specific sites. Which means that they recognize a sequence (recognition site) in the DNA where to cut.

All cells of an organism cannot synthesize all the proteins; only some of them are present in the cell. This means that the proteins are expressed only in some type of cells, which is the result of the differentiation of cells.

Definitions used in this Document:

The term gene is referred to a sequence of DNA that carries the necessary information for the synthesis of a polypeptide or a protein.

Cloning vehicle is a fragment of DNA that it is normally extra-chromosomal and contains some natural sequences of bacterial genome, to allow its replication inside bacteria. Normally present in a circular form.

The term infection is referred to the entrance of an infectious agent into a cell where if the conditions are favorable it can replicate itself and develop.

The term transfection describes a technique in which we can introduce genetic material into a cell using some salts like calcium chloride of salt or by using liposomes.

The expression systems are those which can synthesize a foreign protein in a bacterial cell.

Systems for the introduction of genes into cells or bacterias[2].

Through the use of cloning vectors and with the techniques of transfection, it is possible to introduce genes into a cell and obtain that the genes are efficiently expressed. These vectors can be plasmids or recombinant viruses, which normally are introduced in bacterial systems, mammalian cells, yeast and insect cells. For example the bacteria are expression systems widely used because they can synthesize large quantities of protein at a very low cost, also these systems have been designed to carry on a fast purification of the produced protein. One of the inconveniences about bacteria is that if the protein that it is expressed is unstable inside the cell, it can be degraded rapidly and the yield can go very low. Another disadvantage is that when bacteria are used to express genes from an eucariotic origin (for example genes from mammalian cells) if the protein requires to be modified after its synthesis for its complete biological activity, for example if it needs the addition of carbohydrates (glycosilation) the bacteria is incapable of adding this functional groups that are absolutely essential and so at the end the protein is inactive. Expressing the protein in other systems such as yeast or mammalian cells can solve these products.

Yeast is an excellent expression system for proteins. It is also cheap to grow them and they do not require that the temperature should be maintained at 37° C. for its growth; they can grow at room temperature. As in the case of bacteria, the yeasts are not capable of producing all the modifications that some proteins require after its synthesis (post-translational modification).

The viral vectors such as baculovirus (virus that infect insects), are used today for the expression of many proteins, they also have the advantage that the synthesized protein can be transported outside the cell, which greatly facilitates the purification procedure. Nevertheless the insect cells have a small disadvantage of having only two or three systems for glycosylation, which is required by a certain protein to obtain its complete biological activity.

Other viral vectors such as the viruses belonging to the family of the pox virus (for example vaccinia virus) are used today for the production of protein with biological activity because after infecting a mammalian cell, the proteins that are expressed, all of them posses all the necessary modifications to achieve its normal biological activity.

Which is more important and innovative is that the viruses that are constructed (viral expression vector) are used today for vaccine production as well as for therapeutic and preventive treatment against different types of diseases. Also all these viruses are completely safe and they do not cause any secondary adverse reaction, both in animal and in humans, being characterized as vectors of high efficiency for the development of vaccines.

EXAMPLE 1

Figure 1:
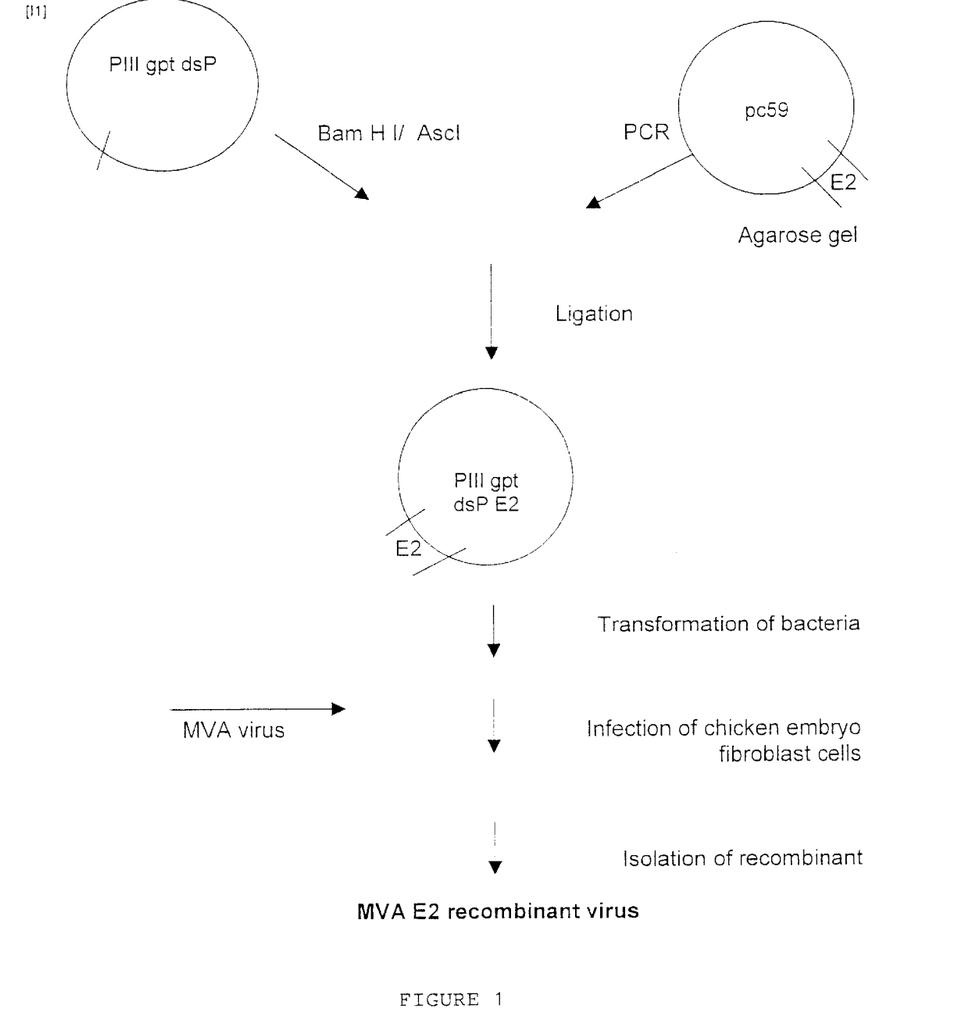
Figure 2:
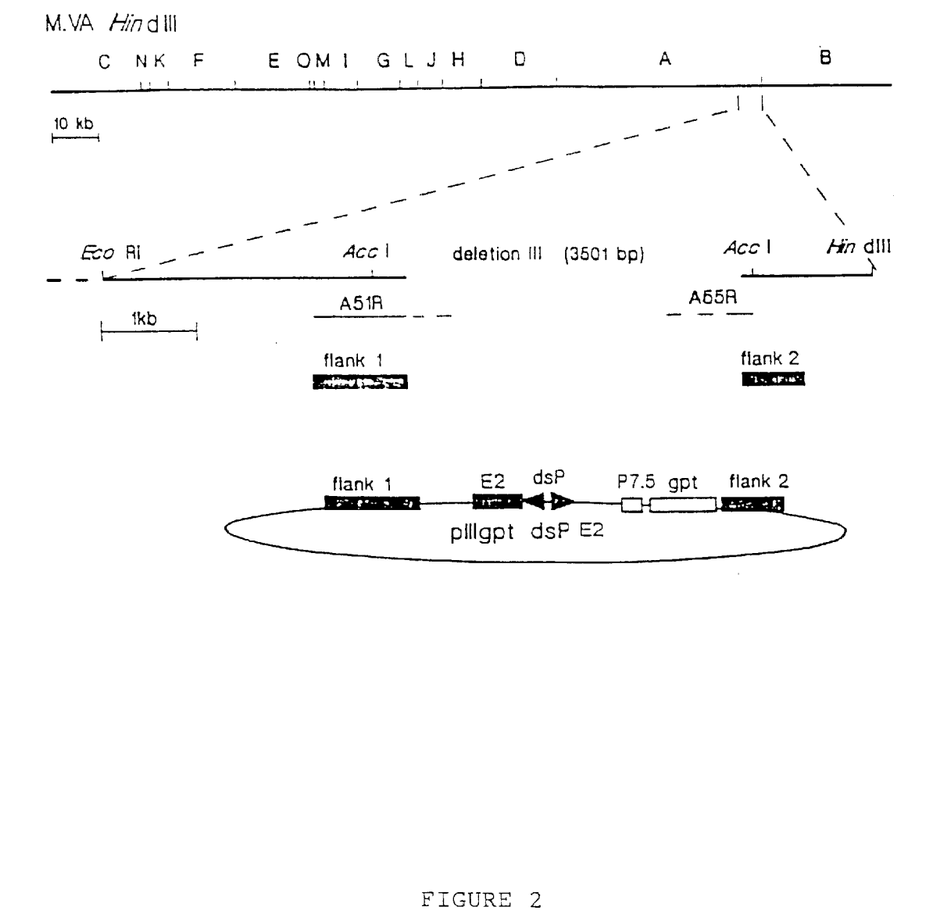

Plasmid construction. A cDNA copy of the bovine papillomavirus E2 gene containing a BamHI site at the start and an AscI site at the end was amplified by the polymerase chain reaction (PCR) using DNA from plasmid pc59 as template. This plasmid contains an open reading frame which cover part of the E1 and E2 genes. A set of primers GS78-CAGCAGGGAT CCAGGATGGAGACAGCATGCGAACGT (SEQ ID NO: 3) and GS79- CAGCAGGCGCGCCCATCATTGGTGGTGCGCCTT (SEQ ID NO: 4) were used to amplify the E2 gene. The PCR product was cloned into the unique BamHI and AscI sites of the pIIIgp dsP plasmid, which carries two copies of the strong synthetic vaccinia virus early/late promoter (FIG. 1). The resulting plasmid (pIII gpt dsp E2) was purified by cesium chloride gradients and used to construct the MVA E2 recombinant virus.

The conditions for PCR were one minute at 55° C., one minute at 72° C. and one minute at 94° C. A PCR machine from Perkin Elmer was used for 30 cycles, the product of the reaction was purified by phenol/chloroform extraction (300 µl of chloroform and 300 µl of phenol) followed by addition of 12 µl of sodium chloride (5M) and 800 µl of ethanol. The tube was kept at −20° C. overnight.

The DNA obtained for the reaction was stored in water at −20° C. The E2 gene was cloned into the plasmid pill gpt dsP. In order to carry out the construction, the plasmid is cut with two restriction enzymes BamHI and AscI in the same buffer of reaction during 2 hours at 37° C. The obtained plasmid was purified by phenol/chloroform extraction followed by precipitation with 12 µl of sodium chloride (5M) and 800 µl of ethanol. The tube was kept at −20° C.

The purified E2 and the cut plasmid were incubated in the presence of T4 ligase (two units per µl). Mixture was incubated at 14° C. overnight (12 hours). The product of the reaction was introduced in E. coli bacteria by electrophoration.

Plasmids from the bacteria were purified by the technique of Miniprep[1] and they were stored at −20° C.

EXAMPLE 2

Construction of Recombinant Virus

To generate MVA E2 recombinant virus, chicken embryo fibroblast cells were infected with MVA virus followed by transfection with the recombinant plasmid pIII gpt dsP E2 using Lipofectin reagent (Gibco, BRL) during 6 hours at 37° C. in a humidified air-5% $CO_2$ atmosphere. 48 hours after infection cells were harvested and processed as described[2]. Recombinant MVA virus expressing the E2 protein were selected by six consecutive rounds of plaque purification of chicken embryo fibroblast cells in the presence of mycophenolic acid. Afterwards the virus were purified by two sucrose 36% gradients using a rotor SW28, 18,000 rpm at 4° C. The recombinant viruses were isolated as a pellet product from the centrifugation step. The pellet was resuspended in 5 ml of saline solution PBS pH 7.4 and the virus solution was kept in aliquots of 500 µl and stored at −70° C. (for details see references 2 and 3).

EXAMPLE 3

Characterization of Recombinant Virus MVA E2

10 µl of MVA E2 virus=2 doses=Approximately $1 \times 10^8$ viral particles is put into a Petri dish, which contains Luria medium without antibiotics. The Petri plates were incubated at 37° C., 24 hours. The presence or absence of bacteria growth was verified the next day.

Normally a good MVA E2 preparation gave no bacterial growth on these plates. The medium Luria composition is for one liter: 10 g of Peptone from Caseine (Difco), 10 g of NaCl and 5 g of yeast extract (Difco).

Titration of recombinant vaccinia MVA E2. 10 $\mu$l of MVA E2 virus were diluted into 1/10, 1/100, 1/1000, 1/10000 in DMEM (10% fetal calf serum). 10 $\mu$l from each dilution is put into 96 wells plates (COSTAR Boxes). After 48–72 hours of infection, the viral plaques are counted on the microscope in order to standardize the doses of the recombinant MVA E2 virus.

Presence of E2 gene in the purified viral particles. Once the MVA E2 virus has been purified, 50 $\mu$l of purified MVA E2 were mixed with 200 $\mu$l of sterile water. 5 $\mu$l of protein K at the concentration of 10 mg/ml was added and incubated for 24 hours at 37° C. 200 $\mu$l of phenol and 300 $\mu$l of chloroform are added and mixed with the vortex, the mixture is centrifuged at 14,000 rpm for 5 minutes. The supernatant was removed and the step is repeated. To the supernatant was added 12 $\mu$l of sodium chloride (5 M) and 800 $\mu$l of ethanol (100% pure). The tubes were kept at −20° C. overnight.

The following tests are carried out (the experimental details are described in references 1 and 2:

EXAMPLE 4

Purification of Recombinant MVA E2 Virus $25 \times 10^6$ chicken embryo fibroblast cells grew at confluence of 85% were infected with MVA E2 recombinant virus, in DMEM medium containing 4% of Fetal Bovine Serum (FBS). The infection was carried out by putting 10 µl of virus for each $10^6$ cells and adding 4 ml of DMEM containing 10% fetal calf serum. The infection was carried out for 1 hour at 37° C. in an incubator with $CO_2$ at 5%. After 10 ml of DMEM (10 FBS) was added to stop the infection.

The infection was kept for 48–72 hours, until all cells were dead.

Cells were collected and centrifuged at 2,500 rpm for 10 minutes.

All viruses collected were resuspended in 20 ml de DMEM (10% fetal calf serum) and stored at −70° C. in a Falcon tube of 50 ml. Afterwards the MVA virus was defrost and homogenized until all cells have been disrupted, this is verified using an optic microscope.

The solution was centrifuged at 300×g for 5 minutes to eliminate nuclei. Supernatant was stored at 4° C. The pellet was resuspended in 5 ml of buffer 10 mM TRIS HCL pH 9, centrifuged again and the supernatant was combined with the previous for 4 times.

The sonicated virus was put on a sucrose 36% gradient, centrifuged at 15,300 rpm for 80 minutes at 4° C. in rotor SW 28.

The supernatant is discarded and the pellet virus was resuspended in 10 ml of buffer 10 mM TRIS HCl pH 9.

The virus was purified again in another sucrose gradient as described above.

The virus pellet was resuspended in 5 ml of buffer PBS pH 7.4 and stored in aliquots of 1 ml. The number of virus particles obtained was verified and stored: one dose of MVA recombinant virus=5 µl, which means 1,000 doses in 5 ml.

The number of virus particles is calculated by measuring the virus solution in a spectrophotometer at 260 nm. One unit of virus at 260 nm is approximately $1.2 \times 10^{10}$ virus/ml, which is equivalent to live virus of $5 \times 10^8$ virus particle forming units (pfu).

Also the number of virus particles is measured by titering the virus on chicken embryo fibroblast cells. The virus plaque on these cells are developed by using a specific antibody against vaccinia virus, and just by counting the number of plaques it is very easy to calculate the titer.

EXAMPLE 5

Expression of the E2 Protein from the MVA E2 Recombinant Virus

Figure 3A:
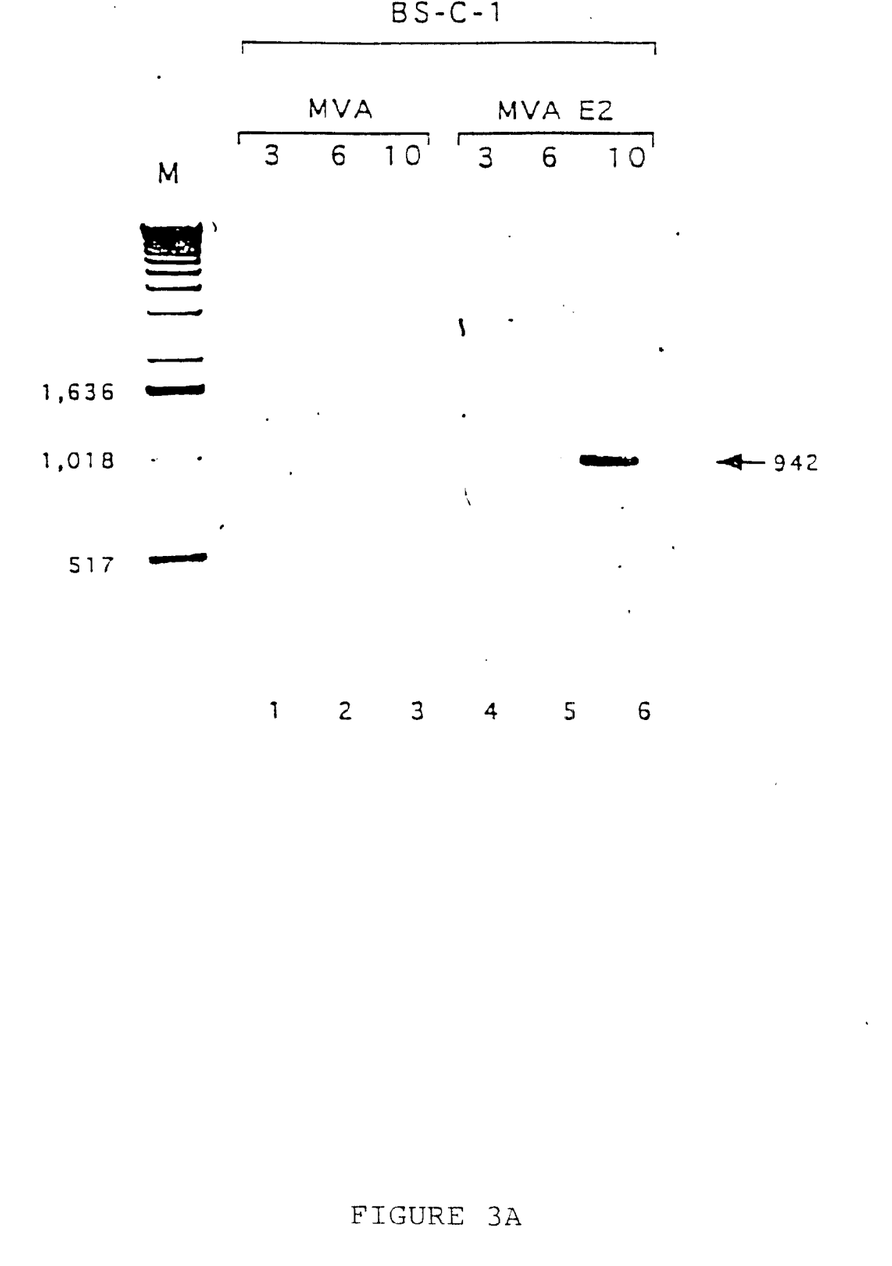

The characterization of the expression of the E2 gene in the MVA E2 recombinant virus was carried out following this procedure. Reverse transcription-PCR analysis was performed to confirm the presence of E2 RNA in Monkey kidney cells (BS-C-1). First-strand products derived from purified total RNA from MBA E2-infected and uninfected BS-C-1 cells were amplified with the primers GS78 and GS79 to give PCR products (of expected sizes) derived from the E2 gene (FIG. 3A). The E2 gene product is 942 bp as shown in FIG. 3A. The experimental procedure was: total RNA (3 µg) from infected cells was isolated, and transcribed with 20 units of avian myeloma virus reverse transcriptase (Boehringer Mannheim, Indianapolis) using 0.5 µg of oligo (dt) 12–18 in a total volume of 50 µl of buffer (50 MM Tris-HCL (pH 8), 70 mM KCl, 10 mM $MgCl_2$, 4 mM dithiothreitol, and 1 mM each of the four deoxy ribonucleoside triphosphates) at 42° C. for 90 minutes. The cDNA product was purified by phenol-chloroform extraction, precipitated with ethanol, and resuspended in 50 µl of water. One µl of cDNA was amplified by 40 cycles of PCR. Primers used for amplification of an internal region of 294 bp within the β-galactosidase gene were: BGR-10 (5'-TCG CGG TGA TGG TGC TGC TGC GTT GG-3') (SEQ ID NO: 1) and BGR-11 (5'-GTTACG ATG CGC CCA TCT ACA CCA A-3') (SEQ ID NO: 2).

A) Stability of E2 RNA.

Figure 3B:
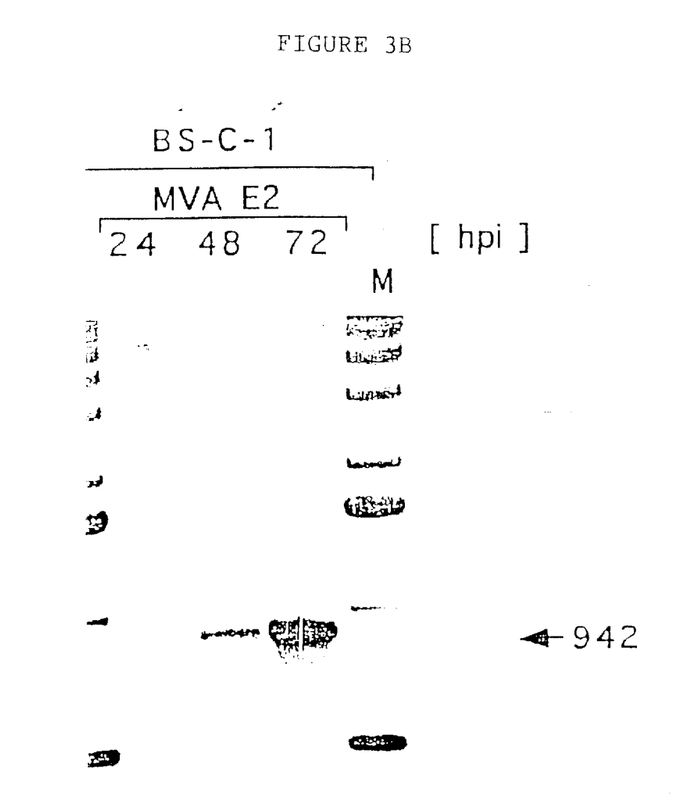

Presence of the E2 RNA was analyzed at different times post infection. E2 RNA was detected by 48 hours of infection, and its product augmented considerably by 72 hours post-infection (FIG. 3B). This result confirmed that MVA E2 was in fact directing the expression of the gene and the synthesis of the papilloma E2 protein in infected cells. These results suggested that there is an accumulation of E2 RNA during infection.

B) Immunoprecipitation.

Figure 3C:
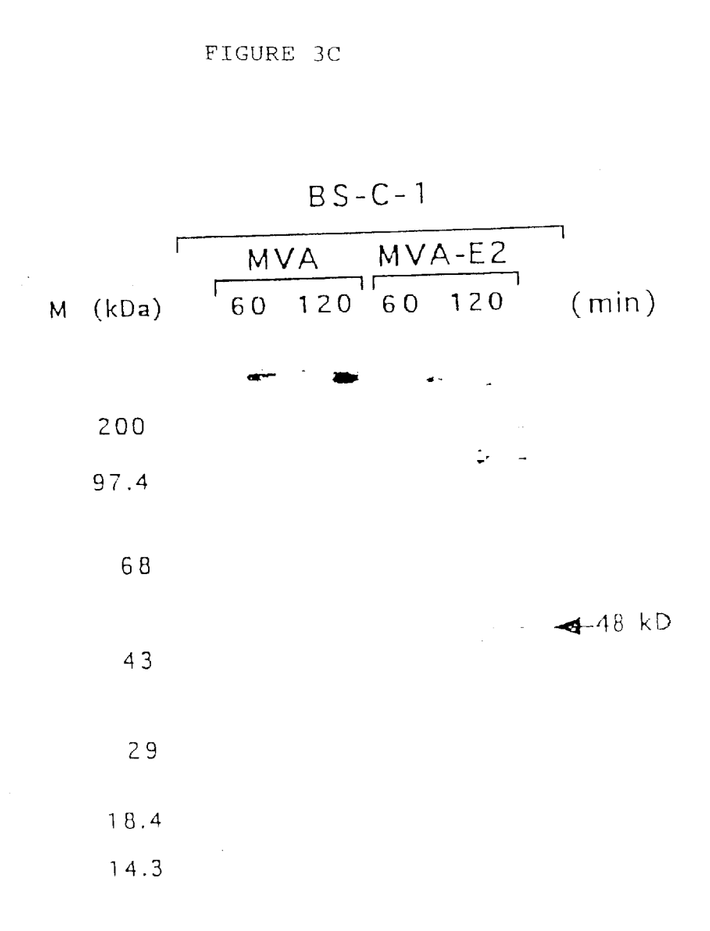

Synthesis of the E2 polypeptide was established by performing metabolic labeling with [$^{35}$S]-methionine of BS-C-1 cells infected with MVA or MVA E2 recombinant virus. In each case the labeled polypeptides are immunoprecipitated with an anti-E2 polyclonal serum. These antibodies reacted specifically with a 48 kDa protein, which corresponds in size to the E2 gene product (FIG. 3C). The experimental procedure was: BS-C-1 cells grown in 12-well plates were infected with MVA o MVA E2 at multiplicity of 15 pfu per cell. Virus were adsorbed during one hour at 37° C. in Dulbecco's modified Eagle's medium (DMEM) with 2% fetal calf serum (FCS). Cultures were then incubated at 37° C. in a 5% $CO_2$ atmosphere. Six hours after infection, the medium was removed, and cultures washed once with one ml of methionine-free MEM. To each well, 0.2 ml of methionine-free MEM supplemented with 50 µCi of [$^{35}$S]-methionine (Dupont, Boston) was added, and incubated during 30 minutes at 37° C. Cytoplasmic extracts of infected cells were prepared by incubating each well in 0.2 ml of 0.5% Nonidet P-40 lysis in buffer (10 mM Tris-HCl, pH 8, 1 mM EDTA) for 10 minutes at 37° C. Total cells extracts were incubated with anti-E2 polyclonal serum for one hour, and protein-antibody complexes immunoprecipitated with 50 µl of Laemmli sample buffer and analyzed by sodium dodecyl sulfate (SDS)-polyacrilamide gel electrophoresis (PAGE) followed by autoradiography.

EXAMPLE 6

Elimination of a Papilloma Tumor from an MVA E2-treated Rabbits

In order to determine the antitumor potential of the recombinant vaccinia virus carrying the papillomavirus E2 gene (MVA E2), New Zealand whites rabbits were transplanted with the VX2 carcinoma. This tumor of rabbit origin can be propagated by successive transplantation into rabbits. When rabbits had a tumor of around 1.5 cm² (approximately 6.7 g), they were inoculated with the control MVA vaccinia virus of the recombinant MVA E2 virus directly into the tumor with $5 \times 10^7$ infectious units of virus. Injections were given once a week during four weeks.

Figure 4A:
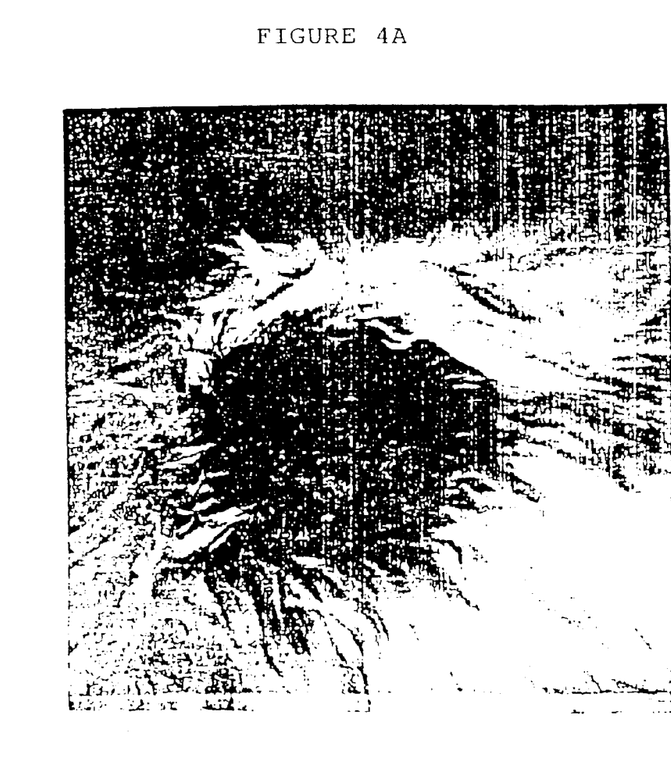
FIG. 4. Elimination of a papilloma tumor from an MVA E2-treated rabbits. VX2 papilloma tumor cells were implanted into the thigh muscle of New Zealand white rabbits. A) Aspect of a rabbit leg at 4 weeks after tumor implantation. B) Same area shown in A, at 8 weeks after MVA E2 treatment.
Figure 4B:
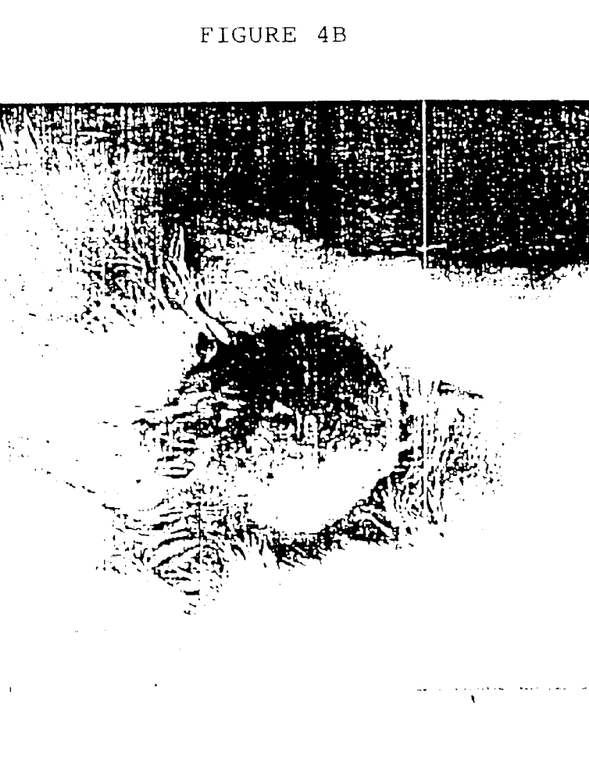
Figure 5A:
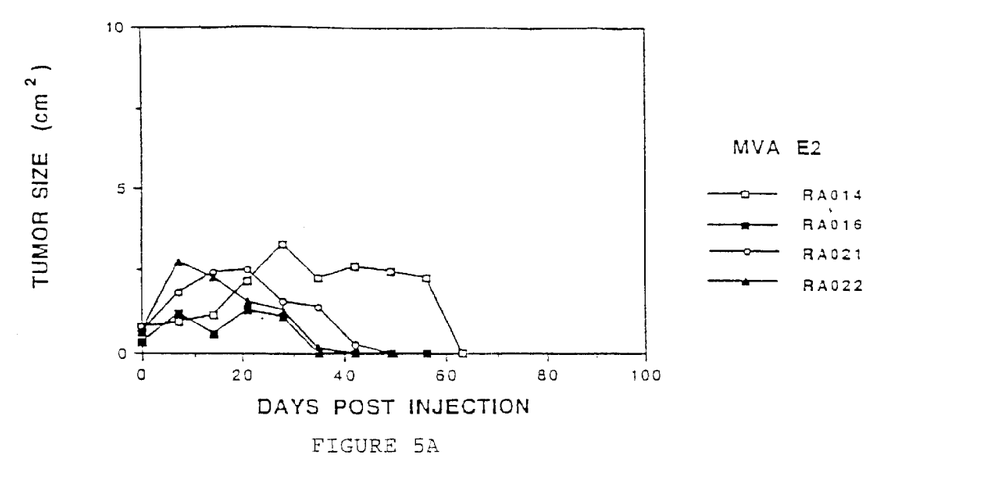
FIG. 5. MVA E2 recombinant vaccinia virus reduces papilloma tumor size. New Zealand rabbits bearing VX2 papilloma tumors (of approximately 1.5 cm$^2$) were inoculated with A) MVA E2 or B) MVA directly into the tumor with 5×10$^7$ infection units/injection, once a week during four weeks. After treatment, animals were then monitored for tumor size. Several representative animals are shown in the graph.
Figure 5B:
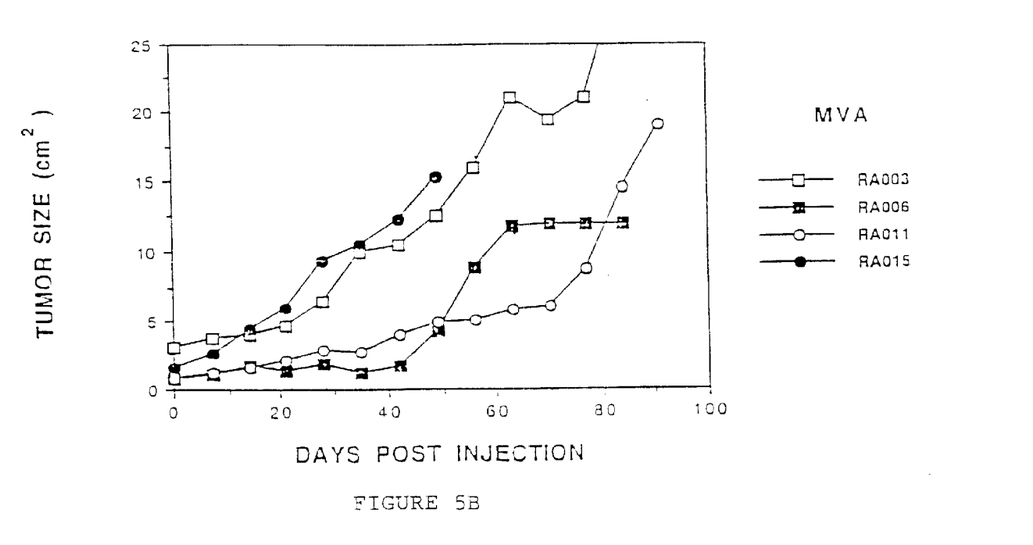

During the anti-tumor therapy, rabbits were monitored for tumor growth every week during one year approximately. Most of the MVA E2-treated animals (80%) showed a steady reduction of tumor size and were free of tumor after two months of treatment (table 1, FIG. 4B and FIG. 5). Complete tumor elimination was taken as positive tumor regression. A small number of MVA E2-treated rabbits were not able to eliminate the tumor (table 1). In contrast, rabbits injected with MVA showed only a very slight reduction in tumor growth (table 1). Interestingly, one rabbit (out of 10) treated with MVA also presented tumor rejection (table 1). Naive rabbits treated with PBS had similar behavior to MVA-treated animals. In both groups tumors kept growing steadily and no significant difference was found between them. These data clearly indicated that treatment with the recombinant virus, MVA E2, is capable of not only reducing papilloma tumor burden but also of inducing complete tumor remission in most animals.

As indicated in table 1, few of the animals that received MVA E2 did not reject the tumor. These rabbits with negative tumor rejection presented an initial improvement in health as reflected in some body weight again, but they finally failed to continue growing, and at about two months after treatment they started to lose weight until they eventually died.

Macroscopic observation of tumor lesions indicated that tumor necrosis was present in most animals treated with the MVA E2 virus, while in MVA-treated animals only a small spot of necrosis was visible. In rabbits, contrary to nude mice, tumors were eliminated completely. These results strongly suggested that tumor regression in rabbits is mediated at least by two mechanisms. First the E2 protein will promote apoptosis in cancer cells where it can be expressed, and second, because vaccinia virus is an excellent vehicle for presentation of antigens to the immune system, it will stimulate the system against infected tumor cells. These additive effects very likely help the immune system to recognize epitopes of specific antigens from cancer cells, which were previously masked from the immune systems. These results suggested that the effect of E2 protein on cells, together with the immune response induced by the vaccinia virus MVA E2 against tumor cells were probably responsible for tumor elimination.

As indicated above, the MVA E2 recombinant virus was capable of inducing tumor regression in most of the rabbits bearing the VX2 tumor. The MVA E-2 treated group presented a rejection frequency of 0.8. In contrast, animals inoculated with the control MVA did not induce elimination of the tumor. In this group the rejection frequency was 0.1 as a result of one individual presenting tumor rejection out of ten that had tumor (table 1). Similarly to control MVA animals, MVA E2-treated animals also showed an increased tumor growth during the first three weeks of treatment. However, in the consecutive weeks they began to show a considerable reduction in tumor size.

These animals had also a better appearance and overall improved health as indicated by the increase in size and gain of body weight. In contrast, animals with no tumor rejection presented a sick appearance and deteriorated rapidly losing much of their body weight. Many of them also died in about three months after the virus treatment.

These data indicated that there is a clear difference between the efficacy of MVA E2 and MVA virus in promoting tumor regression.

EXAMPLE 7

MVA E2 Increases Rabbit Survival of Tumor-bearing Rabbits

Figure 6:
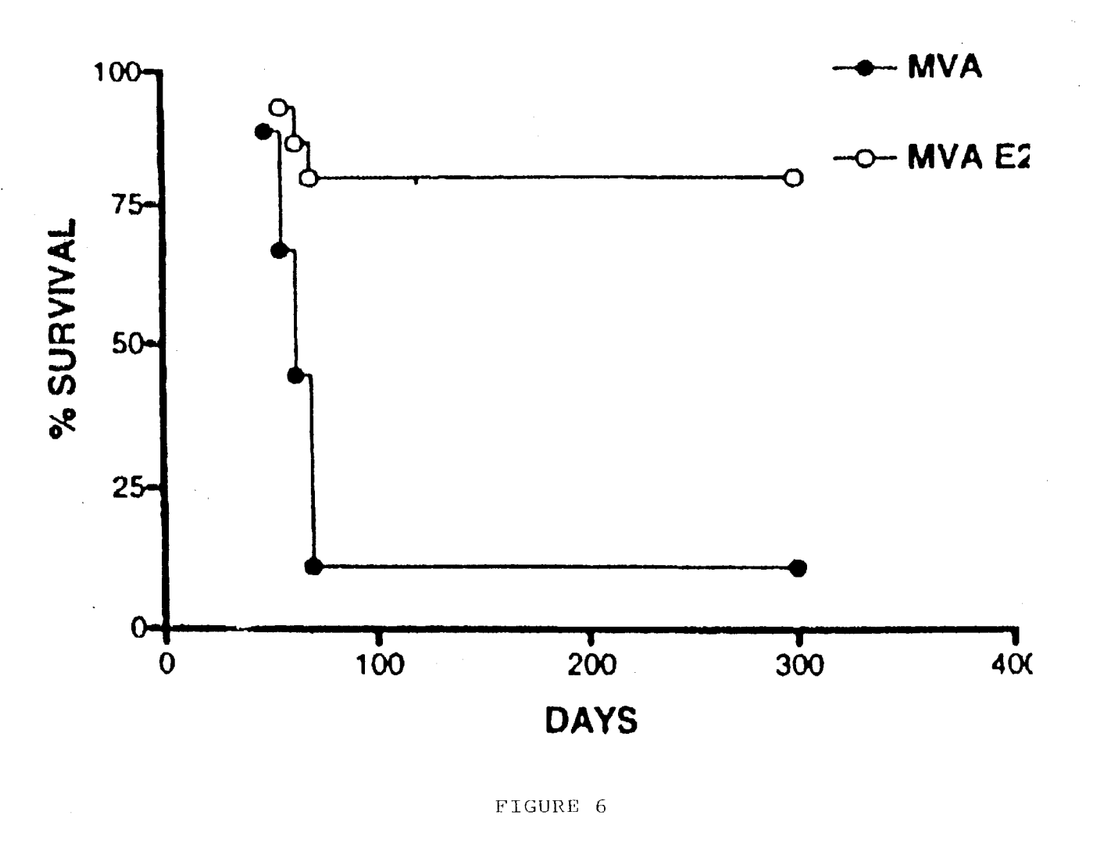

The MVA E2 recombinant virus also increased life expectancy in rabbits bearing tumors. It was observed that all MVA E2-treated animals survived as long as healthy control animals (FIG. 6). Moreover, clinically there was no difference between MVA E2-treated animals and healthy control rabbits. These results strongly suggested that tumor regression was 100% efficient.

Rabbit dissections were performed from the area where the tumor had developed and later regressed after MVA E2 treatment. Macroscopic observations showed the muscle as normal tissue after tumor rejection. It did not present any malformations and it was indistinguishable from the muscle tissue from control healthy animals (data not shown). These results indicated that MVA E2 treatment was very efficient in removing the tumor without affecting the surrounding tissue. High-resolution microscopy of plastic embedded tissue reveals normal distribution of muscle fibers and connective tissue. Perymysion and endomysion have normal size and fibrosis was absent. All functional properties of muscle were also normal as reflected by the normal behavior of all animals. These results suggest that MVA E2 recombinant virus is a safe and non-aggressive anti-tumor therapeutic agent.

EXAMPLE 8

Cellular Immune Response Generated by MVA E2 Recombinant Virus

Normally when infecting with the vaccinia virus a strong cellular and humoral immune response is elicited. The only difference between the native MVA virus and the recombinant MVA E2 is the presence of the papilloma viral protein E2. The results shown above suggest that expression of E2 has given a strong signal to eliminate the tumors. Earlier, it has been demonstrated that the E2 protein is able to promote apoptosis in cancer cells and it is also very likely that the large amount of the E2 protein inside tumor cells promotes cell death. Cell infected with MVA E2 acquire the E2 protein and finally die in about 3 or 4 days. Although infected cells die quickly, it is well known that vaccinia virus is an excellent vehicle for antigen presentation to the immune system and a potent stimulator of immune responses against antigens that normally are not well recognized by the immune systems. So, it is very likely that the MVA E2 infected tumor cells are recognized by the immune system and are inducing a strong immune response against them.

Figure 7:
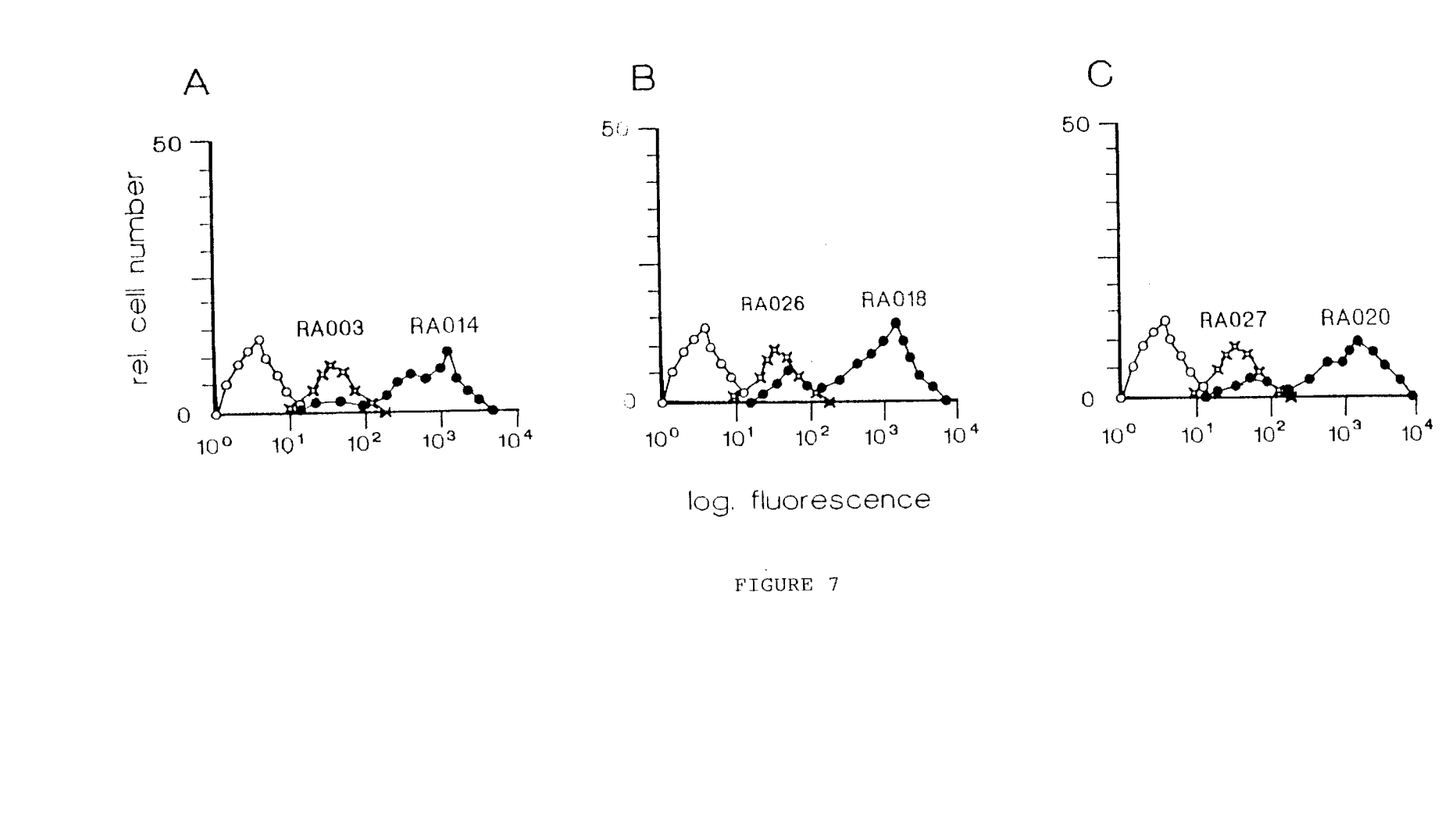
FIG. 7. MVA- and MVA E2-treated rabbits present different anti-papilloma tumor antibodies. VX2 papilloma tumor cells, isolated from freshly dissected tumors, were incubated with different rabbit sera. Rabbit antibodies were detected on the cell surface with a FITC-labeled goat anti-rabbit IgG antibody. Tumor cells were then analyzed by flow cytometry. Naive rabbits (open circles) did not have any anti-tumor antibodies. MVA-treated rabbits, with no tumor regression (crosses) had antibodies that recognized tumor molecules expressed in low levels. MVA E2-treated rabbits, with tumor regression (closed circles) had anti-tumor antibodies that bound to membrane antigens expressed in large amounts. The three panels represent the sera from three MVA-(RA003, RA026, RA027) and three MVA E2-treated rabbits (RA014, RA018, RA020)

In an effort of determine the mechanism of tumor elimination in the MVA E2-treated rabbits. It was decided to look for an immune response against papilloma tumor cells in animal treated with the recombinant vaccinia. Naive rabbits that did not bear the VX2 tumor had no antibodies reacting with these tumor cells. Tumor bearing animals that were inoculated with the control MVA vaccinia virus and that did not show tumor regression presented a small amount of anti-tumor antibodies in their serum (FIG. 7). In contrast, MVA E2-treated animals that showed tumor regression had large amounts of anti-tumor antibodies in circulation (FIG. 7). One mechanism of cell destruction is complement-mediated lysis. The presence of large amounts of anti-tumor antibodies in the MVA E2 treated animals suggested that maybe complement activation was responsible for tumor elimination. It was tested the potential of these anti-tumor antibodies to activate complement and destroy tumor cells, and found that all rabbit sera were unable to induce papilloma tumor cell lysis in the presence of complement.

EXAMPLE 9

Sera Antibodies Stimulate Macrophages, to Mediate Tumor Cell Destruction

Another mechanism for cell destruction is cytotoxicity mediated by activated lymphocytes. Most virus-infected cells induce a strong cellular immune response, so it was possible that the MVA E2 recombinant virus was activating lymphocytes to recognize tumor antigens in tumor cells and to destroy the tumor cells.

Figure 8:
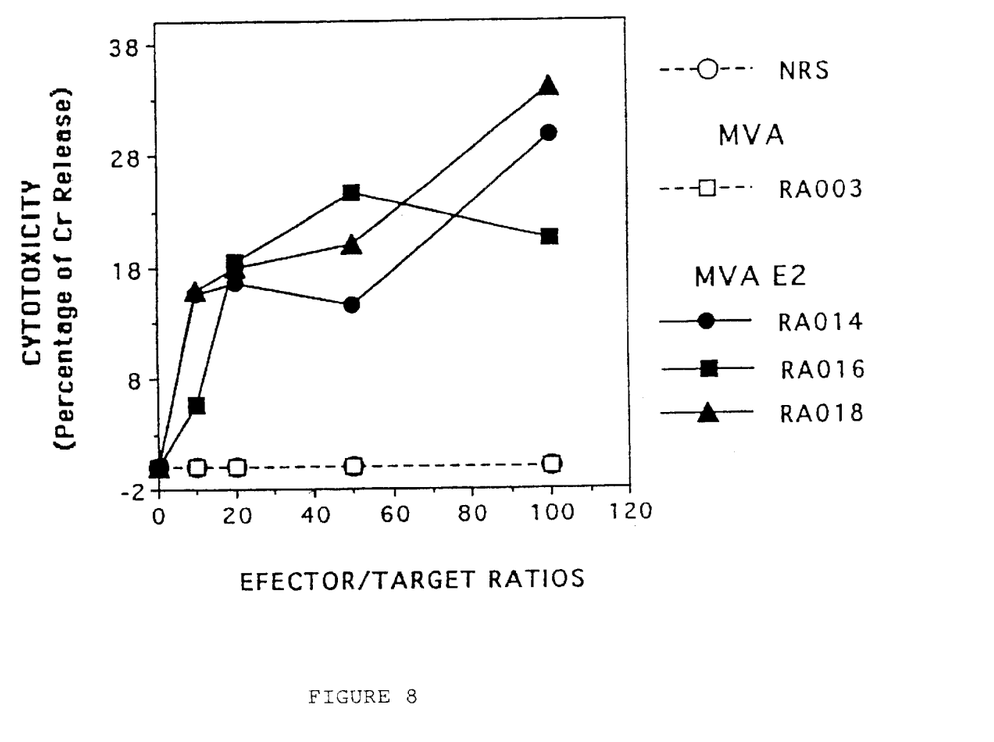
FIG. 8. Sera antibodies stimulate macrophages, to mediate tumor cell destruction. Sera from MVA E-2 treated animals, which had tumor rejection, presented specific killing of the VX2 tumor cells, while sera from MVA-treated animals, with no tumor rejection, showed insignificant cytotoxicity mediated by macrophages.

Sera from MVA E-2 treated animals, which had had tumor rejection, presented specific killing of the VX2 tumor cells, while sera from MVA-treated animals, with no tumor rejection, showed insignificant cytotoxicity mediated by macrophages (FIG. 8). These results strongly suggested that the mechanism of tumor elimination in MVA E2 recombinant vaccinia-treated rabbits is the induction of an immune response that generates anti-tumor antibodies capable of activating effector cells, such as macrophages, to mediate tumor cell destruction.

It was decided to look for the presence of cytotoxic cell in animals that had shown tumor regression. Rabbit lymphocytes were isolated and were tested in an in vitro cytotoxicity assay for their potential to destroy papilloma VX2 tumor cells. These lymphocytes did not kill the target tumor cells at any of the cell/target ratios tested (FIG. 6). In order to determine if there were lymphocytes recognizing the tumor cells directly, we measured the proliferative response of these rabbit lymphocytes. Cells were stimulated in vitro with tumor cells extracts and also with intact tumor cells. In all cases we were unable to detect cell proliferation.

All these results are in complete agreement with the fact that the VX2 tumors can grow in all species of rabbits. Knowing that the animals are non-isogenic, the previous results were not completely surprising and they suggested that the tumor regression mechanism involved other cell types different from lymphocytes.

All references cited in this application are herein incorporated by reference.

LEGEND FIGURES

FIG. 1. Construction of the MVA E2 recombinant virus. Plasmid pIII gpdsP was cut with the restriction enzymes and the plasmid pC59 was incubated with the corresponding oligonucleotides together with the Taq polymerase enzyme in order to amplify the E2 gene by the PCR method. The digest plasmid and the E2 gene were purified and ligated to generate the recombinant plasmid pill gptdsP E2. The pIII gptdsP E2 plasmid was introduced into chicken embryo fibroblast cells (CEF) by transfection followed by the infection with the vaccinia virus MVA. The recombinant MVA E2 virus was purified by six rounds of plaque purification on CEF.

FIG. 2. Schematic map of the MVA genome and the plasmid pIIIgptdsP E2 used for insertion of the bovine papillomavirus E2 gene. HindIII restriction endonuclease sites within the genome of MVA are indicated at the top (kb, kilobase pairs). Letters on the top represent the MVA fragments generated by Hind III digestion. DNA sequences (flank1 and flank 2) adjacent to deletion III within the A fragment of the vaccinia genome were cloned into the plasmid PIIIgptdsP to allow recombination into the MVA genome. A cassette, with back-to-back copies of a strong synthetic vaccinia virus early/late promoter (dsP) is shown. P 7.5 refers to well-characterized vaccinia virus early/late promoter. A cassette with the E2 gene was inserted in front of one of the vaccinia virus early/late promoter. The *E. coli* guanine phosphoribosyl transferase (gpt) gene under control of the P 7.5 promoter is also shown.

FIG. 3. Expression of the E2 gene and production of the E2 protein from MVA E2. (A) Amplification of E2 RNA. Cellular RNA from BS-C-1 cells infected either with MVA (lanes 1–3) or MVA E2 (lanes 4–6) was purified 24 hours after infection. The E2 RNA was amplified by RT-PCR. The quantities, in $\mu$l, of the PCR product are indicated above each lane. An arrow marks the band representing the E2 gene transcript. M represents DNA size markers in bp. (B) E2 RNA accumulation. Cellular RNA from BS-C-1 cells was isolated at different times post infection and processed as described in A. Three $\mu$l of the PCR product were analyzed at 24, 48, and 72 hours post-infection (hpi) on an agarose gel. (C) Immunoprecipitation analysis of cytoplasmic extracts from BS-C-1 cells infected with MVA or MVA E2. At six hours after infection cells were labeled with [$^{35}$S]-methionine for 60 or 120 minutes. Cell lysates were prepared and 50 $\mu$l were immunoprecipitated with an anti-E2 polyclonal antibody. Immunoprecipitates were resolved by SDS-PAGE and autoradiographed. Numbers on the left indicate the position and molecular mass in kilodaltons (kDa) of protein standards. The band representing the E2 protein (48 kDa) is marked by an arrowhead.

FIG. 6. MVA E2-treated rabbits present anti-tumor antibodies that induce macrophage cytotoxicity. VX2 papilloma tumor cells were isolated from freshly dissected tumors and were labeled with $^{51}$Cr for 60 minutes at 37° C. Target tumor cells were then mixed with macrophages at several effector to target rations in the presence of sera from MVA-treated rabbits (RA003), from MVA E2-treated rabbits (RA014, RA016, RA017, RA018, RA020), or from naive rabbits (NRS). After a five-hour incubation the supernatants were collected and the amount of $^{51}$Cr released was determined in a gamma counter. All MVA-treated animals present identical curves to the one shown. For the MVA E2-treated group just few representative animals are shown.

TABLE 1

Tumor rejection in animals treated with MVA or MVA E2 recombinant

| Virus administered | Route | Animals showing tumor rejection[1] | Total number of animals | Rejection frequency[2] |
|---|---|---|---|---|
| MVA | I.T. | 1 | 10 | 0.1 |
| MVAE2 | I.T. | 12 | 15 | 0.8 |

New Zealand white rabbits containing VX2 tumors (~1.5 cm$^2$ ~6.7 grams*) were inoculated with MVA or MVA E2, into tumor with 5 × 10$^7$ infectious units/injection, once a week for four weeks.
I.T. Intratumoral
[1] It is defined as complete tumor elimation.
[2] Calculated as: animals showing tumor rejection/total number of animals
*The tumor weight was taken as the main value of three different tumors, which were isolated from different rabbits.

New Zealand white rabbits containing VX2 tumors (~1.5 cm$^2$~6.7 grams*) were inoculated with MVA or MVA E2, into tumor with 5×10$^7$ infectious units/injection, once a week for four weeks.

REFERENCES

1. Glick, B. R. y J. J. Pasternak, Molecular Biotechnology: Principles and Applications of Recombinant DNA, American Society for Microbiology, Washington, D.C., 1998.
2. Stiegler, G., G. Burkland y P. Buckel, Biotecnología de f ármacos, Investigación y Ciencia, 254, 52–61, 1997.
3. Beaudenon, S., D. Kremdorf, S. Obalek, S. Jablonska, G. Pehau-Arnaudet O. Croissant and G. Orth (1978). Plurality of genital human papillomaviruses: characterization of two new types with distinct biological properties Virology, 161: 374–384.
4. Beaudenon, S., D. Kremsdorf, O. Croissant, S. Jablonska, S. Wain-Hobson and G. Orth (1986). A novel type papillomavirus associated with genital neoplasias. Nature 321: 246–249.
5. Dürst, M., L. Gissman, H. Ikenberg and H. A. zur Hausen (1983). Papillomavirus DNA from a cervical carcinoma and its prevalence in cancer bioposy samples from different geographic regions. Proc. Natl. Aced. Sci. USA 80: 3812–3815.
6. Lörincz A. T., G. F. Temple, R. J. Kurman, A. B. Jenson and W. D. Lancaster (1987). Oncogenic association of specific human papillomavirus type with cervical neoplasia. JNCI 79: 671–677.
7. Lörincz, A. T., W. Quinn, Lancaster and G. F. Temple (1987). A new type of papillomavirus associated with cancer of the uterine cervix. Virology 159: 198–190.
8. Cullen, A. P., Reid, R., Campion, M. and Lörincz, A. (1991). Analysis of the physical state of different human papillomavirus DNAs in intraephitelial and invasive cervical neoplasm, J. Virol. 65: 606–612.
9. Lörincz, A. T., A. P. Quinn, W. D. Lancaster and G. F. Temple (1987). A new type of papillomavirus associated with cancer of the uterine cervix. Virology 63: 2829–2834.
10. Reid, R., m. Greenberg, A. B. Jenson, M. Husain, J. Willet, Y. Daoud, G. Temple, C. Stanhope, A. Sherman, G. Phibbs and A. Lörincz (1987). Sexually transmitted papillomavirus infections I. The anatomic distribution and pathologic grade of neoplastic lesions associated with different viral types. Am. J. Obstet. Gynecol. 156: 212–222.
11. Romanczuk, H., Thierry, F. and Howley, P. M. (1990). Mutational analysis of ci elements involved in E2 modulation of human papillomavirus type 16P$_{97}$ and type 18P$_{105}$ promoters. J. Virol. 64: 2849–2859.
12. De Villiers, E. M. (1994). Human pathogenic papillomavirus types: an update. Curr. Top. Microbiol. Immunol. 186: 1–12.
13. Matsukura, T., S. Koi and M. Sugase (1989). Both episomal and integrated forms of human papillomavirus type 16 are involved in invasive cervical cancer. Virology 172, 63–72.
14. Nagahashfar, Z. S., N. B. Rosenshein, A. T. Lörincz, J. Buscema and K. V. Shah (1987). Characterization of human papillomavirus type 45, a new type 18-related virus of the genital tract. J. Gen. Virol. 68: 3073–3079.
15. Hwang, E. S., D. J. Riese, J. Settleman, C. A. Nilson, J. Honig, S. Flynn and D. DiMaio (1993). Inhibition of cervical carcinoma cell line proliferation by the introduction of a bovine papillomavirus regulatory gene. J. Virol. 67: 3720–3729.
16. Berumen, J., Casas, L., Segura, E., Amezcua, J. And Garcia-Carranca, A. (1994). Genoma amplification of human papillomavirus types 16 and 18 in cervical carcinomas in related to the retention of E1/E2 genes. Int. J. Cancer 56: 640–645.
17. Fuchs, P., F. Girardi, and H. Pfister (1989). Human papillomavirus 16 DNA in cervical cancer and in lymph nodes of cervical cancer patients: a diagnostic marker for early metastases?. Int. J. Cancer 43: 41–44.
18. He, Y. And L. Huang (1997). Growth inhibitor of human papillomavirus 16 DNA-positive mouse tumor by antisense RNA transcribed from U6 promoter. Cancer Res. 57: 3933–3999.
19. Steele, C., L. M. Cowsert and E. J. Shillitoe (1993). Effects of human papillomavirus type 18-specific antisense oligonucleotides on the transformed phenotype of human carcinoma cell lines. Cancer Res. 53: 2330–2337.
20. Tan, I. M. C. and R. C. Y. Ting (1995). In vitro and in vivo inhibition of human papillomavirus type 16 E6 and E7 genes. Cancer Res. 55: 2330–2337.
21. Chamberlain, R. S., M. Carrol, V. Bronte, P. Hwu, S. Warren, J. C. Yang, M. Nishimura, B. Moss, S. A. Rosenberg and N. P. Restifo (1996). Coestimulation enhances the active immunotherapy effect of recombinant anticancer vaccines. Cancer Res. 56: 2832–2836.
22. Azuma, M., D. Ito, H. Yagita, K. Okumura, J. H. Phillips, L. L. Lanier and C. Somoza (1993). B70 antigen is a second ligand for CTLA-4 and CD28. Nature 366: 76–79.
23. Freeman, G. J., G. S. Gray, C. D. Gimmi, D. B. Lombard, L. J. Zhou, M. White, J. D. Fingeroth, J. G. Gribben and L. M. Nadler (1991). Structure, expression and T cell costimulatory activity of the murine homologue of the human B lymphocyte activation antigen B7. J. Exp. Med. 174: 625–631.
24. Linsley, P. S., W. Brady, L. Grosmaire, A. Aruffo, N. K. Damle and J. A. Ledbetter 81991). Binding of the B cell activation antigen B7 to CD28 costimulates T cell proliferation and interleukin 2 mRNA accumulation. J. Exp. Med. 173: 721–730.
25. Desaintes, C., C. Demeret, S. Goyat, M. Yaniv and F. Thierry (1997). Expression of the papillomavirus E2 protein in HeLa cells leads to apoptosis. EMBO. J. 16: 504–514.
26. Dowhanick, J. J., A. A. McBride and P. M. Howley (1995). Supression of cellular proliferation by the papillomavirus E2 protein. J. Virol. 69: 7791–7799.
27. Selvakumar, R., L. A. Borenstein, Y. L. Lin, R. Ahmed and F. O. Wettstein (1995). Immunization with non-structural proteins E1 and E2 cottontail rabbit papillomavirus stimulates regression of virus-induced papillomas. *J. Virol.* 69: 602–605.
28. Binns, M. M. and G. L. Smith (1993). Recombinant Poxvirus. ACR Press, Boca Raton, Fla., USA.
29. Perkus, M. E., A. Piccini, B. R. Lipinskas and E. Paoletti (1985). Recombinant vaccinia virus: immunization against multiple pathogens. *Science* 229: 981.
30. Fenner, F., Henderson, D. A., Arita, I., Jezek, Z. And Ladnyi, I. D. (1988). Smallpox and its eradication (WHO/Geneva), pp. 539–592.
31. Mayr, A., Stickl, H., Muller, H. K., Danner, K. And Singer H. (1978). Zbl. Bakt. Hyg., I, *Abt. Orig. B.* 167: 375–390.
32. Stickl, H., Hochstein-Mintzel, V. Mayr, A. Huber, H. C. Schafer, H. And Holzner, A. (1974). *Dtsch. Med. Wochenschr.* 99: 2386–2392.
33. Sutter, G. and Moss, B. (1992). Non replicating vaccinia vector efficiently expresses recombinant genes. *Proc. Natl. Acad. Sci.* 89: 10847-1085.
34. Sutter, G., Ohlmann, M. And Erfle, V. (1995). Non-replicating vaccinia ector efficiently expresses bactercophoge T7 RNA polymerase, *FEBS Letters* 371: 9–12.
35. Lathe, R., Kieny, M. P., Gerlinger, P., Clertant, P., Guizani, I., Cuzin, F. and Chambon, P. (1987). Tumor prevention and rejection with recombinant vaccinia. *Nature* 326: 878–880.
36. Sutter, G., L. S. Wyatt, P. L. Foley, J. R. Bennick and B. Moss (1994). A recombinant vector derived from the host range-restricted and highly attenuated MVA strain of vaccinia virus stimulates protective immunity in mice to influenza virus. *Vaccine* 12: 53–59.
37. Yang, Yu-Chung, Okayama, H., Howley, P. (1985). Bovine Papillomavirus contains multiple transforming genes. Proc. Natl. Acad. Sci. Vol. 82. ppp 1030–1034.
38. Valadez, G. V., Sutter, G., Garcia Carranca., Jose, Marco-V., Erfle, V., Norma, G., Merchant, H, and Rosales, R. (2000). The highly attenuatted MVA strain of vaccinia virus carrying the E2 gene of bovine papillomavirus is able to stop growth of human tumors generated in nude mice. Cancer 88 (7): 1650–1662.
39. Rosales, C., Valadez-Graham V., Arrellin, G., Merchant, H., and Rosales R. (2000). MVA E2 a Recombinant Vaccinia Containing the papilloma Virus E2 Protein Promotes Tumor Regression By Stimulating Macrophage Antibody-Dependent Cytotoxicity. Cancer Immunology Immunotherapy. 49 (7): 347–360

What is claimed is:

1. A recombinant Modified Vaccinia Ankara (MVA) virus, comprising: a DNA sequence encoding a bovine papillomavirus E2 (BPV E2) protein.

2. The recombinant MVA virus according to claim 1, wherein said DNA sequence is inserted into a site of naturally occurring deletions within the MVA genome.

3. The recombinant MVA according to claim 1, wherein said DNA sequence is under transcriptional control of the vaccinia virus early/late promoter p7.5.

4. A composition comprising:
a recombinant MVA according to claim 1; and
a pharmaceutically acceptable carrier or diluent.

5. A composition comprising:
a recombinant MVA according to claim 3; and
a pharmaceutically acceptable carrier or diluent.

6. A method for the treatment of lesions generated by papillomavirus infections, comprising:
administering a therapeutically effective amount of a recombinant MVA according to claim 1 to a living animal in need thereof.

7. The method according to claim 6, wherein said living animal is a human.

8. The method according to claim 6, wherein
(a) said lesion is a tumor lesion,
(b) said recombinant MVA expresses the E2 gene of bovine papillomavirus, and
(c) said recombinant MVA is administered directly to said tumor.

9. A method of inducing anti-tumor antibodies in a tumor-bearing animal, comprising:
administering a recombinant MVA according to claim 1 to said tumor-bearing animal.

10. A method of producing a recombinant virus, comprising:
carrying out homologous recombination between virus MVA and a transfer vector comprising a papillomavirus E2 gene under the control of the vaccinia p7.5 promoter; and
isolating the recombinant virus.

11. A method for inducing the regression of cancer tumors by the repression of the E6 and E7 oncoproteins, comprising:
administering a therapeutically effective amount of the recombinant MVA according to claim 1 directly to the tumor cells of a living animal in need thereof.

12. A method for inducing apoptosis in cancer cells, comprising:
administering a therapeutically effective amount of the recombinant MVA according to claim 1 directly to the cancer cells of a living animal in need thereof.

13. The method according to claim 6, wherein
(a) said lesion is a pre-cancer lesion,
(b) said recombinant MVA expresses the E2 gene of bovine papillomavirus, and
(c) said recombinant MVA is administered directly to said tumor.

14. A method for the treatment of lesions generated by papillomavirus infections, comprising:
administering a therapeutically effective amount of a recombinant Modified Vaccinia Ankara (MVA) virus comprising a sequence encoding a papillomavirus E2 protein to a living animal in need thereof.

* * * * *

SEQUENCE LISTING

```
<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: BGR-10 primer targeted to the
      Beta-galactosidase gene

<400> SEQUENCE: 1
tcgcggtgat ggtgctgctg cgttgg                                    26

<210> SEQ ID NO 2
<211> LENGTH: 25
<212> TYPE: DNA
<213> ORGANISM: Artificial Sequence
<220> FEATURE:
<223> OTHER INFORMATION: BGR-11 primer targeted to the
      Beta-galactosidase gene

<400> SEQUENCE: 2
gttacgatgc gcccatctac accaa                                     25

<210> SEQ ID NO 3
<211> LENGTH: 36
<212> TYPE: DNA
<213> ORGANISM: Artificial Sequence
<220> FEATURE:
<223> OTHER INFORMATION: GS78 primer targeted to Bovine papillomavirus.

<400> SEQUENCE: 3
cagcagggat ccaggatgga gacagcatgc gaacgt                         36

<210> SEQ ID NO 4
<211> LENGTH: 33
<212> TYPE: DNA
<213> ORGANISM: Artificial Sequence
<220> FEATURE:
```

-continued

<223> OTHER INFORMATION: GS79 primer targeted to Bovine papillomavirus.

<400> SEQUENCE: 4
cagcaggcgc gcccatcatt ggtggtgcgc ctt                33